(12) United States Patent
Xue et al.

(10) Patent No.: US 12,215,372 B2
(45) Date of Patent: Feb. 4, 2025

(54) METHOD FOR ASYMMETRICALLY PREPARING L-PHOSPHINOTHRICIN BY OXIDATION-REDUCTION REACTION THROUGH BIOLOGICAL MULTI-ENZYME COUPLING

(71) Applicant: ZHEJIANG UNIVERSITY OF TECHNOLOGY, Hangzhou (CN)

(72) Inventors: Yaping Xue, Hangzhou (CN); Feng Cheng, Hangzhou (CN); Liuyu Wang, Hangzhou (CN); Yuguo Zheng, Hangzhou (CN); Jianmiao Xu, Hangzhou (CN); Shuping Zou, Hangzhou (CN)

(73) Assignee: ZHEJIANG UNIVERSITY OF TECHNOLOGY, Hangzhou (CN)

( * ) Notice: Subject to any disclaimer, the term of this patent is extended or adjusted under 35 U.S.C. 154(b) by 478 days.

(21) Appl. No.: 17/607,371

(22) PCT Filed: Jun. 8, 2020

(86) PCT No.: PCT/CN2020/094841
§ 371 (c)(1),
(2) Date: Oct. 28, 2021

(87) PCT Pub. No.: WO2021/184557
PCT Pub. Date: Sep. 23, 2021

(65) Prior Publication Data
US 2022/0220516 A1    Jul. 14, 2022

(30) Foreign Application Priority Data
Mar. 18, 2020  (CN) .......................... 202010192774.4

(51) Int. Cl.
| C12P 7/52 | (2006.01) |
| C12N 1/20 | (2006.01) |
| C12N 9/06 | (2006.01) |
| C12N 9/10 | (2006.01) |
| C12N 15/52 | (2006.01) |
| C12N 15/70 | (2006.01) |

(52) U.S. Cl.
CPC .................. *C12P 7/52* (2013.01); *C12N 1/20* (2013.01); *C12N 9/0024* (2013.01); *C12N 9/1096* (2013.01); *C12N 15/52* (2013.01); *C12N 15/70* (2013.01); *C12Y 104/03003* (2013.01); *C12Y 206/01019* (2013.01); *C12N 2511/00* (2013.01); *C12N 2800/101* (2013.01)

(58) Field of Classification Search
CPC .......... C12P 7/52; C12N 1/20; C12N 9/0024; C12N 9/1096; C12N 15/52; C12N 15/70; C12N 2511/00; C12N 2800/101; C12Y 104/03003; C12Y 206/01019
See application file for complete search history.

(56) References Cited

U.S. PATENT DOCUMENTS

2017/0253897 A1* 9/2017 Green ..................... C12P 13/04

FOREIGN PATENT DOCUMENTS

| CN | 107502647 | 12/2017 |
| CN | 109072261 | 12/2018 |
| CN | 109576236 | 4/2019 |
| CN | 109609582 | 4/2019 |
| CN | 110055289 | 7/2019 |

OTHER PUBLICATIONS

Tkavc, et al. "Prospects for Fungal Bioremediation of Acidic Radioactive Waste Sites: Characterization and Genome Sequence of Rhodotorula taiwanensis MD1149." Frontiers in Microbiology. (Year: 2017).*

Transcript: POY70719 EnsemblFungi Rhodotorula taiwanensis str. MD1149, <https://fungi.ensembl.org/Rhodotorula_taiwanensis_gca_002922495/Transcript/Sequence_Protein?db=core;g=BMF94_6129;r=RTAI_MD1149_contig_97:8414-10297;t=POY70719;tl=czLJnf9yAhS8NuWx-22797014> Retrieved Jan. 8, 2024. (Year: 2017).*

Bordo and Argos. "Suggestions for "Safe" Residue Substitutions in Site-directed Mutagenesis" J. Mol. Biol. 217, 721-729. (Year: 1991).*

(Continued)

*Primary Examiner* — Suzanne M Noakes
*Assistant Examiner* — Ciara A McKnight
(74) *Attorney, Agent, or Firm* — Jiwen Chen; Joywin IP Law PLLC

(57) ABSTRACT

A method for asymmetrically preparing L-phosphinothricin by oxidation-reduction reaction through biological multienzyme coupling, where D,L-phosphinothricin as a raw material is catalyzed by an enzyme catalysis system to obtain L-phosphinothricin, wherein the enzyme catalysis system comprises a D-amino acid oxidase mutant for catalyzing D-phosphinothricin in D,L-phosphinothricin into 2-carbonyl-4-[hydroxy(methyl)phosphono] butyric acid and a transaminase for catalytic reduction of the 2-carbonyl-4-[hydroxy(methyl)phosphono] butyric acid into L-phosphinothricin; the D-amino acid oxidase mutant is obtained by mutation of D-amino acid oxidase in wild strain *Rhodotorula taiwanensis* at one of the following sites: (1) M213S-N54V-F58E; (2) M213S-N54V-F58E-D207A; (3) M213S-N54V-F58E-D207A-S60T. According to the present invention, the D-amino acid oxidase mutant provides better catalytic efficiency, and when racemic D,L-phosphinothricin is used as a substrate for catalytic reaction, the conversion rate is much higher than that of the wild type enzyme, and the PPO yield is also greatly improved.

10 Claims, 1 Drawing Sheet
Specification includes a Sequence Listing.

(56) References Cited

OTHER PUBLICATIONS

Pontrelli et al., "*Escherichia coli* as a host for metabolic engineering." Metabolic Engineering, 50: 16-46. (Year: 2018).*
GenBank Accession No. POY70719, Feb. 7, 2018.

* cited by examiner

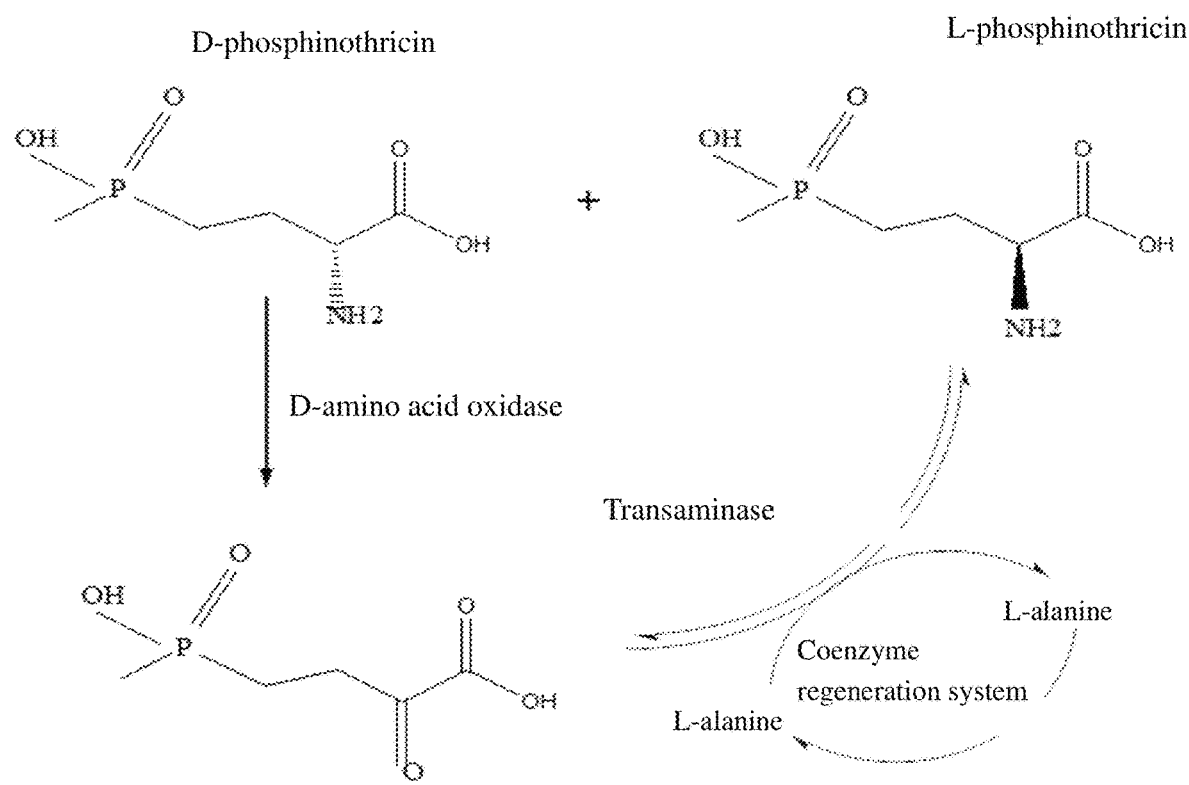

METHOD FOR ASYMMETRICALLY PREPARING L-PHOSPHINOTHRICIN BY OXIDATION-REDUCTION REACTION THROUGH BIOLOGICAL MULTI-ENZYME COUPLING

This is a U.S. national stage application of PCT Application No. PCT/CN2020/094841 under 35 U.S.C. 371, filed Jun. 8, 2020 in Chinese, claiming priority to Chinese Patent Applications No. 202010192774.4, filed Mar. 18, 2020, all of which are hereby incorporated by reference.

Applicant hereby electronically submits the Sequence Listing in ASCII text file (CRF format) with the file name of P76186US0_SEQ_LIST_ST25.txt, created on Oct. 28, 2021 and with the size of 24,576 bytes, which is hereby incorporated by reference. It is respectfully submitted that the Sequence Listing in CRF format does not include new matter. In addition, the Sequence Listings hereby submitted satisfy both the paper copy requirement under 37 CFR 1.821 (c) and the computer-readable form requirement of 37 CFR 1.182 (e). Thus, the requirement of 37 CFR 1.821 (f) has been satisfied.

FIELD OF TECHNOLOGY

The present invention relates to the field of biotechnology, in particular to a method for asymmetrically preparing L-phosphinothricin by oxidation-reduction reaction through biological multi-enzyme coupling.

BACKGROUND TECHNOLOGY

Phosphinothricin (PPT for short), also known as glufosinate ammonium, with a chemical name of 2-amino-4-[hydroxy(methyl)phosphono]butyric acid, is the second largest herbicide tolerant for transgenic crops in the world and was developed and produced by Hoechst (which is now owned by Bayer after several mergers). Phosphinothricin, a phosphonate herbicide, is a glutamine synthetase inhibitor and a non-selective (biocidal) contact herbicide.

It is well known that the market for non-selective biocides is huge. At present, the three major herbicides in the world include paraquat, glyphosate, and phosphinothricin. In terms of market share, glyphosate ranks the first, but due to its long-term use, a large number of weeds have become resistant against it, and glyphosate tends to lose efficacy. Paraquat has been listed under the Rotterdam Convention due to its high toxicity and is banned or restricted in an increasing number of countries worldwide; and the Ministry of Agriculture of China issued a notice stating that paraquat production would be ceased as of 1 Jul. 2014 and banned as of 1 Jul. 2016. At present, the output of phosphinothricin is small yield, but phosphinothricin exhibits excellent herbicidal performance and less phytotoxicity and side effects, therefore, it has great market potential in the future.

Phosphinothricin consists of two optical isomers, L-phosphinothricin and D-phosphinothricin. However, only L-phosphinothricin has herbicidal activity, and it is easily decomposed in the soil, with less toxicity to humans and animals, and has a wide herbicidal spectrum, and small destructive effect on the environment.

Phosphinothricin currently available on the market is generally a racemic mixture. If the phosphinothricin product can be used as a pure optical isomer in the L-configuration, the consumption of phosphinothricin can be remarkably reduced, which is of great significance for improving atomic economy, reducing use cost and reducing environmental pressure.

There are three main methods for preparing chiral pure L-phosphinothricin: chiral resolution method, chemical synthesis method and bio-catalysis method.

The chiral resolution method is to separate the D-form and L-form isomers by chiral resolution of racemic D,L-phosphinothricin or its derivatives, thus obtaining the optically pure L-phosphinothricin. This process mainly has the following shortcomings: expensive chiral resolution reagents are needed, the theoretical yield can only reach 50%, the single resolution rate is low, and the process is relatively complex.

The chemical synthesis method is to synthesize optically pure L-phosphinothricin from chiral raw materials. The chemical asymmetric synthesis method has many process steps, low yield and high production cost due to expensive chiral raw materials, which are not conducive to large-scale preparation of L-phosphinothricin.

The bio-catalysis method for the production of phosphinothricin has the advantages of strict stereoselectivity, mild reaction conditions, high yield and the like, and is an advantageous method for producing L-phosphinothricin. It mainly includes the following three categories:

(1) With L-phosphinothricin derivatives as substrates, L-phosphinothricin is obtained through direct hydrolysis by an enzyme method. Its main advantages include high conversion rate and high ee value of the product; however, expensive and difficult-to-obtain chiral raw materials are needed as precursors.

(2) With racemic phosphinothricin precursor as the substrate, L-phosphinothricin is obtained by selective resolution with enzymes. Its main advantages are that raw materials are relatively easy to obtain, and the activity of the catalyst is high, but its theoretical yield can only reach 50%, thereby causing waste of raw materials.

(3) With D,L-phosphinothricin as the raw material, D-phosphinothricin is catalyzed by D-amino acid oxidase to obtain L-phosphinothricin precursor 2-carbonyl-4-[hydroxy(methyl)phosphono]butyric acid (PPO for short), which is then catalyzed with transaminase to obtain L-phosphinothricin.

The decomposition of L-phosphinothricin into 2-carbonyl-4-[hydroxy(methyl)phosphono]butyric acid has been found as early as in the study of the metabolic pathway of phosphinothricin in soil microorganisms. Therefore, it is a good method to produce L-phosphinothricin by reversible enzyme catalysis using 2-carbonyl-4-[hydroxy(methyl)phosphono]butyric acid as the substrate.

D-amino acid oxidase is a kind of enzyme that specifically and selectively catalyzes D-amino acid and its derivatives to generate α-keto acid, and the reaction is catalyzed and completed by its own coenzyme FAD. Due to its excellent catalytic efficiency and selectivity, D-amino acid oxidase is widely used in the production of L-amino acid and α-keto acid through biological resolution. For example, D-amino acid oxidase converts cephalosporin C to glutaryl-7-aminocephalosporanic acid.

Transaminases are pyridoxal phosphate (PLP)-dependent enzymes which are transferases that catalyze the exchange of amino and keto groups. They widely exist in nature and play an important role in amino transfer in the process of nitrogen metabolism in cells. Transaminases have many advantages, such as high enantioselectivity and regioselectivity, high reaction rate and stability. Transamination is a reversible reaction, and 2-carbonyl-4-[hydroxy(methyl)

phosphono]butyric acid can generate L-phosphinothricin through a reverse reaction as catalyzed by transaminases.

SUMMARY OF THE INVENTION

In view of the defects in the prior art, the present invention provides a brand-new method for preparing L-phosphinothricin by resolving the racemic mixture. Meanwhile, the present invention provides a D-amino acid oxidase mutant which has high activity of catalyzing D-phosphinothricin to react to generate 2-carbonyl-4-[hydroxy(methyl) phosphono]butyric acid.

The present invention provides a method for asymmetrically preparing L-phosphinothricin by oxidation-reduction reaction through biological multi-enzyme coupling, where D,L-phosphinothricin as a raw material is catalyzed by an enzyme catalysis system to obtain L-phosphinothricin, wherein the enzyme catalysis system comprises a D-amino acid oxidase mutant for catalyzing D-phosphinothricin in D,L-phosphinothricin into 2-carbonyL-4-[hydroxy(methyl) phosphono]butyric acid and a transaminase for catalytic reduction of the 2-carbonyl-4-[hydroxy(methyl)phosphono] butyric acid into L-phosphinothricin, and The D-amino acid oxidase mutant is obtained by mutation of D-amino acid oxidase in wild strain *Rhodotorula taiwanensis* at one of the following four sites:
(1) M213S;
(2) M213S-N54V-F58E;
(3) M213S-N54V-F58E-D207A;
(4) M213S-N54V-F58E-D207A-S60T.

The specific principles are as follows. Using a one-pot multi-enzyme catalytic system, with racemic D,L-phosphinothricin as a substrate, D-phosphinothricin is catalyzed into 2-carbonyL-4-[hydroxy(methyl)phosphono]butyric acid by D-amino acid oxidase. Meanwhile, the catalase added is used for removing by-product hydrogen peroxide, because accumulation of hydrogen peroxide can poison the catalyst. L-phosphinothricin does not participate in the reaction and is completely retained. Then, the 2-carbonyl-4-[hydroxy (methyl)phosphono]butyric acid is reduced into L-phosphinothricin as catalyzed by transaminases, thereby realizing in-situ racemization of D,L-phosphinothricin to obtain optically pure L-phosphinothricin. Pyridoxal phosphate is used as coenzyme and amino donor as co-substrate for transaminase catalysis.

Transaminases in the present application may employ sequences conventional in the art. Preferably, the amino acid sequence of the transaminase is as shown in SEQ ID No. 7.

For catalyzing D-phosphinothricin to react to generate 2-carbonyl-4-[hydroxy(methyl)phosphono]butyric acid, the expressed crude enzyme liquid or the expressed purified enzyme liquid can be used, and the catalytic reaction can also be directly carried out by using recombinant bacteria capable of expressing the D-amino acid oxidase mutant. Similarly, for the transaminase, the expressed crude enzyme liquid, the expressed purified pure enzyme liquid can be used, or recombinant bacteria capable of expressing the transaminase can be directly used.

More preferably, the D-amino acid oxidase mutant is obtained by adding a recombinant bacterium expressing the D-amino acid oxidase mutant in a reaction system;

The transaminase is obtained by adding a recombinant bacterium expressing the transaminase together with a coenzyme pyridoxal phosphate into the reaction system.

More preferably, *E. coli* BL21(DE3) is used as a host cell for both of the recombinant bacteria.

More preferably, in the reaction system, the D,L-phosphinothricin has a final concentration of 100-400 mM, the recombinant bacterium expressing the D-amino acid oxidase mutant is added at an amount of 20-40 g/L, the catalase has a concentration of 0.1 g/L, the recombinant bacterium expressing the transaminase is added at an amount of 30-50 g/L, and the coenzyme pyridoxal phosphate has a concentration of 1 mM. The reaction is carried out at a temperature of 30° C. and a pH of 8 for 10 hours.

After the reaction is completed, the final product L-phosphinothricin is separated and extracted by pretreatment-ion exchange-crystallization.

The present invention further provides a D-amino acid oxidase mutant obtained by mutation of D-amino acid oxidase in wild-type *Rhodotorula taiwanensis* at one of the following four sites:
(1) M213S;
(2) M213S-N54V-F58E;
(3) M213S-N54V-F58E-D207A;
(4) M213S-N54V-F58E-D207A-S60T.

The present invention also provides a gene encoding the D-amino acid oxidase mutant, wherein the gene has a nucleotide sequence as shown in one of SEQ ID No. 3 to 6.

The present invention also provides a recombinant bacterium comprising the gene.

Compared with the prior art, the present invention has the following beneficial effects:
(1) The D-amino acid oxidase mutant of the present invention has better catalytic efficiency, and when racemic D,L-phosphinothricin is used as a substrate for catalytic reaction, the conversion rate is much higher than that of the wild type enzyme, and the yield of PPO is also greatly improved.
(2) In the present invention, with racemic D,L-phosphinothricin as a substrate, D-phosphinothricin is oxidized into 2-carbonyl-4-[hydroxy(methyl)phosphono]butyric acid by using D-amino acid oxidase, and L-phosphinothricin is completely reserved because it does not participate in the reaction; the product 2-carbonyl-4-[hydroxy(methyl)phosphono]butyric acid can be further reduced into L-phosphinothricin as catalyzed by transaminases, thereby realizing in-situ racemization of D,L-phosphinothricin. On the contrary, the traditional oxidation method needs to convert both D-phosphinothricin and L-phosphinothricin into 2-carbonyl-4-[hydroxy(methyl)phosphono]butyric acid, causing the waste of raw materials.
(3) The present invention can directly take D,L-phosphinothricin as a substrate for resolution, does not require expensive resolution reagents, does not need to synthesize phosphinothricin derivatives, and does not need to carry out the steps of separation, re-racemization, re-resolution and the like on the D-phosphinothricin.
(4) The method of the present invention overcomes the defect in synthesis of the L-phosphinothricin precursor 2-carbonyl-4-[hydroxy(methyl)phosphono]butyric acid by the chemical method, is a green, environment-friendly and low-carbon process route, and is suitable for large-scale industrial production and application.

BRIEF DESCRIPTION OF THE DRAWINGS

FIG. 1 is a reaction formula for producing L-phosphinothricin by resolution with the multi-enzyme system adopted in the method of the present invention.

DETAILED DESCRIPTION OF THE EMBODIMENTS

Reagents for upstream genetic engineering: the genome extraction kit, plasmid extraction kit, and DNA purification and recovery kit used in the examples of the present invention were purchased from Corning Life Sciences (Wujiang) Co., Ltd.; E. coli DH5α, E. coli BL21 (DE3), plasmid pET-24a(+) were purchased from Shanghai Xuguan Biotechnology Development Co., Ltd.; DNA marker, low-molecular-weight standard protein, and protein gel were purchased from Beijing GenStar Co., Ltd.; and the primer synthesis and sequencing were completed by Hangzhou TSINGKE Biological Technology Co., Ltd. For the use of the above reagents, refer to the corresponding product instructions.

The reagent used in the downstream catalytic process, 2-carbonyl-4-[hydroxy(methyl)phosphono]butyric acid (PPO for short), was synthesized in the laboratory; D,L-phosphinothricin was purchased from Sigma-Aldrich; other commonly used reagents were purchased from Sinopharm Chemical Reagent Co., Ltd.

The structural formula of D-phosphinothricin (D-PPT for short) is as shown in Formula (1); the structural formula of L-phosphinothricin (L-PPT for short) is as shown in Formula (2); the structural formula of 2-carbonyl-4-[hydroxy(methyl)phosphono]butyric acid (PPO for short) is as shown in Formula (3).

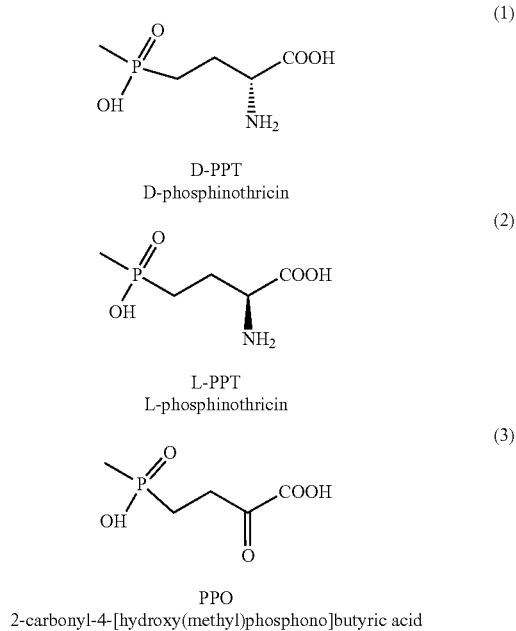

(1) D-PPT
D-phosphinothricin (2) L-PPT
L-phosphinothricin (3) PPO
2-carbonyl-4-[hydroxy(methyl)phosphono]butyric acid The reaction formula for D-phosphinothricin to produce 2-carbonyl-4-[hydroxy(methyl)phosphono]butyric acid, ammonia and hydrogen peroxide as catalyzed by D-amino acid oxidase is as shown in FIG. 1.

The present invention detected the progress of the reaction and analyzed the product by high performance liquid chromatography (HPLC). HPLC analysis: chromatographic column/AQ-C18; column temperature/30° C.; flow rate/1 mL/min; detection wavelength/205 nm; mobile phase: 50 mM $(NH_4)_2HPO_4$, to which 1% of 10% tetrabutyl ammonium bromide in water was added, pH adjusted to 3.8 with phosphoric acid, and 12% of acetonitrile was added.

The content of phosphinothricin of either configuration was examined by chiral HPLC analysis which comprised: chromatographic column//Pntulips QS-C18; mobile phase/ 50 mM ammonium acetate solution:methanol=9:1; detection wavelength/338 nm; flow rate/1 mL/min; column temperature/30° C. Derivatization reagent: 0.1 g of o-phthalaldehyde and 0.12 g GN-acetyl-L-cysteine were separately weighed and 10 ml of ethanol was added to facilitate dissolving, followed by addition of 40 mL of 0.1 M boric acid buffer (pH 9.8). The mixture was shaken to fully dissolve, and stored in a refrigerator at 4° C. for later use (not more than 3 days). Derivatization reaction and determination: 200 μL of the sample was mixed with 400 μL of the derivatization reagent at 30° C. for 5 minutes, and then mixed with 400 μL of ultra-pure water. Then, 10 μL of the sample was injected for analysis.

Example 1

Construction and Screening of D-Amino Acid Oxidase Mutant Library

1. Construction of Recombinant Bacteria

The gene sequence of D-amino acid oxidase (Gen Bank No.: POY70719.1) derived from *Rhodotorula taiwanensis* was sent to Sangon Biotech (Shanghai) Co., Ltd. for whole-gene synthesis after codon optimization and cloned into the recombinant expression plasmid pET-24a(+). The recombinant plasmid was transferred to the expression host *E. coli* BL21 (DE3) after sequencing verification, for subsequent use in expression of recombinant D-amino acid oxidase. The gene sequence of the D-amino acid oxidase after codon optimization is as shown in SEQ ID No. 2.

2. Construction of D-Amino Acid Oxidase Mutant Library

In the first round, with the D-amino acid oxidase gene with optimized codons obtained by the above whole gene synthesis as a template, and using the primers used for mutations of M213R and M213S in Table 1 respectively, site-specific mutation PCR was carried out, followed by transformation and plating. The dominant strain obtained by screening was a mutant with M213S mutation, and the plasmid of the dominant mutant was named as D-amino acid oxidase mutant pRtDAAO-M213S.

In the second round, with the mutant pRtDAAO-M213S as a template, and using the primers for mutations of N54G, N54L, N54V and N54A in Table 1 respectively, site-directed mutation PCR was carried out, followed by transformation and plating. The dominant strain obtained through screening was a mutant with double mutations of M213S and N54V, and the plasmid of the dominant mutant was named as D-amino acid oxidase mutant pRtDAAO-M213S-N54V.

In the third round, with the mutant pRtDAAO-M213R-N54V as a template, and using the primers used for mutations of F58E, F58A, F58R and F58S in Table 1 respectively, site-directed mutation PCR was carried out, followed by transformation and plating. The dominant strain obtained by screening was a mutant with three mutations of M213S, N54V and F58E, and the plasmid of the dominant mutant was named as D-amino acid oxidase mutant pRtDAAO-M213S-N54V-F58E.

In the fourth round, with the mutant pRtDAAO-M213S-N54V-F58E as a template, using the primers used for mutations of D207A, D207T and D207E in Table 1 respectively, site-directed mutation PCR was carried out, followed by transformation and plating. The dominant strain obtained by screening carried four mutations of M213S, N54V, F58E and D207A, and the plasmid of the dominant mutant was named as D-amino acid oxidase mutant pRtDAAO-M213R-N54V-F58E-D207A.

In the fifth round, with the mutant pRtDAAO-M213S-N54V-F58E-D207A as a template, and using the primers used for mutations of S60A, S60E and S60T in Table 1 respectively, site-directed mutation PCR was carried out, followed by transformation and plating. The dominant strains obtained by screening carried five mutations of M213S, N54V, F58E, D207A and S60T, and the plasmid of the dominant mutant was named as D-amino acid oxidase mutant pRtDAAO-M213S-N54V-F58E-D207A-S60T. The dominant single mutants in the later experiments were all constructed by the same method.

Specifically, the PCR reaction system is as follow:
2×Phanta Max buffer: 25 µL;
dNTPs: 1 µL;
Upstream primer: 1 µL;
Downstream primer: 1 µL;
Template: 1 µL;
Phanta Super-Fidelity DNA polymerase: 0.5 µL;
ddH$_2$O: 20.5 µL.

PCR reaction conditions: pre-denaturation at 95° C. for 5 minutes; denaturation at 95° C. for 15 seconds, annealing at 56° C. for 30 seconds, and elongation at 72° C. for 6 minutes, with a total of 30 cycles; post-elongation at 72° C. for 10 minutes; storage at 4° C.

DNA agarose gel electrophoresis was performed for positive verification of PCR results, and the results showed that the amplified products were single bands, with the size of about 1300 bp, respectively. The PCR product was treated with Dpn I enzyme to digest the template, and the amplification product was purified and recovered by a DNA recovery and purification kit. For the specific steps, refer to the purification kit instructions.

TABLE 1

| Mutation | Primer name | Primer sequence (5'-3') |
|---|---|---|
| M213S | M213S-Pf | CGTTGCACCTCTGACAGCAGCGATCCGAAC |
|  | M213S-Pr | CGCTGCTGTCAGAGGTGCAACGTTTGCA |
| M213R | M213R-Pf | CGTTGCACCCGTGACAGCAGCGATCCGAAC |
|  | M213R-Pr | CGCTGCTGTCACGGGTGCAACGTTTGCA |
| N54V | N54V-Pf | CGGGTGCGGTTTGGACCCCGGAAATGAGCAAGGAA |
|  | N54V-Pr | ATTTCCGGGGTCCAAACCGCACCCGCCCACGGGCT |
| N54G | N54G-Pf | CGGGTGCGGGTTGGACCCCGGAAATGAGCAAGGAA |
|  | N54G-Pr | ATTTCCGGGGTCCAACCCGCACCCGCCCACGGGCT |
| N54L | N54L-Pf | CGGGTGCGCTTTGGACCCCGGAAATGAGCAAGGAA |
|  | N54L-Pr | ATTTCCGGGGTCCAAAGCGCACCCGCCCACGGGCT |
| N54A | N54A-Pf | CGGGTGCGGCTTGGACCCCGGAAATGAGCAAGGAA |
|  | N54A-Pr | ATTTCCGGGGTCCAAGCCGCACCCGCCCACGGGCT |
| F58E | F58E-Pf | GACCCCGGAAATGAGCAAGGAAGACGG |
|  | F58E-Pr | CTTGCTCATTTCCGGGGTCCAAACCGC |
| F58A | F58A-Pf | GACCCCGGCTATGAGCAAGGAAGACGG |
|  | F58A-Pr | CTTGCTCATAGCCGGGGTCCAAACCGC |

TABLE 1-continued

| Mutation | Primer name | Primer sequence (5'-3') |
|---|---|---|
| F58R | F58R-Pf | GACCCCGCGTATGAGCAAGGAAGACGG |
|  | F58R-Pr | CTTGCTCATACGCGGGGTCCAAACCGC |
| F58S | F58S-Pf | GACCCCGTCGATGAGCAAGGAAGACGG |
|  | F58S-Pr | CTTGCTCATCGACGGGGTCCAAACCGC |
| D207A | D207A-Pf | GTGAAGAGCGCTTGCAAACGTTGCACCTCT |
|  | D207A-Pr | CAACGTTTGCAAGCGCTCTTCACCAGAAC |
| D207T | D207T-Pf | GTGAAGAGCACGTGCAAACGTTGCACCTCT |
|  | D207T-Pr | CAACGTTTGCACGTGCTCTTCACCAGAAC |
| D207E | D207E-Pf | GTGAAGAGCGAGTGCAAACGTTGCACCTCT |
|  | D207E-Pr | CAACGTTTGCACTCGCTCTTCACCAGAAC |
| S60T | S60T-Pf | CCGGAAATGACTAAGGAAGACGGTCCGCGT |
|  | S60T-Pr | GTCTTCCTTAGTCATTTCCGGGGTCCAAAC |
| S60A | S60A-Pf | CCGGAAATGGCTAAGGAAGACGGTCCGCGT |
|  | S60A-Pr | GTCTTCCTTAGCCATTTCCGGGGTCCAAAC |
| S60E | S60E-Pf | CCGGAAATGGAGAAGGAAGACGGTCCGCGT |
|  | S60E-Pr | GTCTTCCTTCTCCATTTCCGGGGTCCAAAC |

Example 2

Construction of Recombinant Bacterium Expressing Transaminase

1. Amplification of Target Gene Transaminase

The transaminase gene was cloned from the genome of *Pseudomonas* sp. and the corresponding PCR upstream and downstream primers were designed based on the corresponding genomic DNA sequence (GenBank Accession No.: WP_076423369.1).

Upstream primer: ATGAACACCAACAACGCTC

Downstream Primer: TTAAGCCTGTTTAGCTTC

PCR amplification system:
2×Phanta Max buffer: 25 µL;
dNTPs: 1 µL;
Upstream primer: 1 µL;
Downstream primer: 1 µL;
Template: 1 µL;
Phanta Super-Fidelity DNA polymerase: 0.5 µL;
ddH$_2$O: 20.5 µL.

PCR reaction conditions: pre-denaturation at 95° C. for 5 minutes; denaturation at 95° C. for 30 seconds, annealing at 60° C. for 30 seconds, and elongation at 72° C. for 6 minutes, with a total of 30 cycles; post-elongation at 72° C. for 10 minutes; storage at 4° C.

DNA agarose gel electrophoresis was performed for positive verification of PCR results, and the results showed that the amplified products were single bands, with the size of about 1300 bp, respectively. The PCR product was treated with Dpn I enzyme to digest the template, and the amplification product was purified and recovered by a DNA recovery and purification kit. For the specific steps, references were made to the purification kit instructions.

2. Construction of Expression Vector and Engineered Bacteria

The expression vector pET-28a(+) and PCR amplification products were double-cleaved with the corresponding restriction enzymes, respectively, and the cleaved products were purified and recovered by a DNA purification kit after enzyme cleavage to remove the restriction enzymes and the digested nucleotide small fragments. The PCR amplification product after double enzyme digestion was connected to expression vector pET-28a(+) with a corresponding incision by T4 DNA ligase to construct expression vector pET-28a (+)-gabT. The constructed expression vector was transformed into *E. coli* BL21 (DE3), coated on an LB plate containing 50 mg/ml kanamycin resistance, and cultured at 37° C. for 8-12 hours. The cloned and extracted plasmids were randomly selected and sequenced for identification, and the recombinant *E. coli* BL21 (DE)/pET-28a(+)-gabT expressing the recombinant plasmid pET-28a (+)-gabT was screened.

Example 3

Culture of Microorganisms

1. Culture of Bacterial Cells

Engineered bacteria containing D-amino acid oxidase gene and transaminase gene were activated by plate streaking, and single colonies were selected and inoculated into 10 mL of LB liquid medium containing 50 μg/mL kanamycin, and cultured under shaking at 37° C. for 10 hours. The samples were transferred at an inoculation amount of 2% to 50 mL of LB liquid medium also containing 50 μg/mL kanamycin, and cultured under shaking at 37° C. until $OD_{600}$ reached about 0.8. Thereafter, IPTG with a final concentration of 0.5 mM was added and the mixture was cultured under shaking at 28° C. for 12 hours. After culture, the culture solution was centrifuged at 8,000 rpm for 10 minutes, the supernatant was discarded, and the cells were collected and stored in an ultra-low temperature refrigerator at −80° C. for later use.

2. Preparation of Crude Enzyme Liquid

The collected bacterial cells after culture were washed twice with phosphate buffer (50 mM) at pH 8, and then the cells were re-suspended in PBS (50 mM) with pH=8 and ultrasonicated for 30 times under the conditions of a powder of 400 W for 2 seconds with an internal of 5 seconds. The fragmented cell suspension was centrifuged a 4° C. and 8,000 rpm for 10 minutes, the precipitate was removed, and the resultant supernatant was the crude enzyme liquid.

3. Purification of Enzyme

The crude enzyme liquid was combined with Ni affinity chromatography resin balanced with a loading buffer (50 mM phosphate buffer with pH=8, containing 500 mM NaCl and 20 mM imidazole), then rinsed with a rinsing buffer (50 mM phosphate buffer with pH=8, containing 50 mM imidazole and 500 mM NaCl) until essentially free of foreign proteins, and subsequently eluted with an elution buffer (50 mM phosphate buffer with pH=8, containing 200 mM imidazole and 500 mM NaCl), and the target proteins were collected. After purity identification by electrophoresis, the target proteins were combined and dialyzed against a dialysis buffer (50 mM phosphate buffer with pH=8) for 24 hours. The trapped solution had a protein content of 2.7 mg/mL as determined by the Coomassie brilliant blue method, and the enzyme liquid was diluted to a final concentration of 0.5 mg/mL, sub-packaged and cryopreserved at −80° C., thereby obtaining the recombinant pure enzyme.

Each of the D-amino acid oxidase mutants was also prepared as described above.

Example 4

Determination of D-Amino Acid Oxidase Activity

Definition of enzyme activity: According to the regulation of the 1961 International Enzymology Conference, one enzyme activity unit refers to the amount of enzyme that transforms one micromolar of substrate or one micromolar of related groups in the transformed substrate within one minute under specific conditions (30° C.).

Determination of enzyme activity of D-amino acid oxidase: 400 μl of a substrate solution (50 mM D, L-phosphinothricin) dissolved in 50 mM phosphate buffer was placed in a metal bath oscillator and kept at 30° C. for 10 minutes. Then 50 μl of pure enzyme and 0.25 μl of catalase (Sigma-Aldrich, Art. No. 60634) were added, and timing was started. The reaction was carried out at 30° C. for 10 minutes, 5 μL of 6 M hydrochloric acid was added thereto, the mixture was taken out, shaken and mixed evenly, and then the reaction was terminated. The mixture was centrifuged at 12,000 rpm for 3 min and the supernatant was 2-fold diluted with deionized water for HPLC detection. Enzyme activity was calculated based on the concentration of 2-carbonyl-4-[hydroxy(methyl)phosphono]butyric acid determined by HPLC. The results are shown in Table 2.

TABLE 2

| Enzyme activity determination results | | |
|---|---|---|
| Number | Mutation type | Enzyme activity (U/L) |
| Control 1 | Non-mutation | 0.23 |
| E1 | M213S | 0.78 |
| E2 | M213S-N54V-F58E | 3.21 |
| E3 | M213S-N54V-F58E-D207A | 3.89 |
| E4 | M213S-N54V-F58E-D207A-S60T | 4.63 |

Determination of transaminase activity: 400 μl of substrate solution (50 mM 2-carbonyl-4-[hydroxy(methyl) phosphono]butyric acid) dissolved in 50 mM phosphate buffer was placed in a metal bath oscillator, kept at 30° C. for 10 minutes, 50 μl of pure enzyme, 1 mM PLP and 80 mM L-alanine were added, and timing was started. The reaction was carried out at 30° C. for 10 minutes, 5 μL of 6 M hydrochloric acid was added, the mixture was taken out, shaken and mixed evenly, and then the reaction was terminated. The mixture was centrifuged at 12,000 rpm for 3 minutes, the supernatant was 2-fold diluted with deionized water, and detected by HPLC. The enzyme activity was calculated based on the L-phosphinothricin concentration measured by HPLC.

Example 4

Large-Scale Preparation of Bacterial Cells

Since a large amount of biocatalyst is required in the process of producing L-phosphinothricin, large-scale preparation of bacterial cells is required. The medium used was LB medium.

A glycerol tube containing the recombinant D-amino acid oxidase engineered bacterium was activated by plate streaking, and then single colonies were selected and inoculated into a 50 mL LB liquid medium containing 50 μg/mL kanamycin, and cultured under shaking at 37° C. for 12 hours. The sample was transferred at an inoculation amount of 2% to 1 L of fresh LB liquid medium also containing 50 μg/mL kanamycin, and cultured under shaking at 37° C. until $OD_{600}$ reached about 0.8. Thereafter, IPTG with a final concentration of 0.5 mM was added and the mixture was cultured under shaking at 28° C. for 16 hours. After the culture, the culture solution was centrifuged at 8,000 rpm for 10 minutes, the supernatant was discarded, and the cells were collected and stored in an ultra-low temperature refrigerator at −80° C. for later use.

Example 5

Preparation of L-Phosphinothricin Using D-Amino Acid Oxidase Mutant (E1) and Transaminase Recombinant bacteria capable of expressing D-amino acid oxidase (E1) and transaminase were cultured in the same manner as in Example 4, and the bacterial cells were collected by centrifugation.

D,L-phosphinothricin was quantitatively weighed into a 50 mM phosphate buffer with pH=8 and placed into a reactor, so that the final concentration of D,L-phosphinothricin was 100 mM, the D-amino acid oxidase (E1) cell concentration was 20 g/L, the catalase concentration was 0.1 g/L, and the transaminase cell concentration was 30 g/L. 400 mM L-alanine and 1 mM PLP were added. The reaction temperature was controlled at 30° C. by a water bath. PPO production was detected by achiral liquid chromatography with timing sampling. Also, the decrease of D-PPT and increase and ee value of L-PPT were detected by pre-column derivatization high performance liquid chromatography.

At the end of 10 hours of reaction, 41.36 mM D-PPT remained, with conversion of 7.33% (the maximum theoretical conversion is 50%), and 58.77 mM L-PPT was generated (ee 99%).

Example 6

Preparation of L-Phosphinothricin Using D-Amino Acid Oxidase Mutant (E2) and Transaminase.

Recombinant bacteria capable of expressing D-amino acid oxidase (E2) and transaminase were cultured in the same manner as in Example 4, and the bacterial cells were collected by centrifugation.

D,L-phosphinothricin was quantitatively weighed into a 50 mM phosphate buffer with pH=8 and placed into a reactor, so that the final concentration of D,L-phosphinothricin was 100 mM, the D-amino acid oxidase (E2) cell concentration was 20 g/L, the catalase concentration was 0.1 g/L, and the transaminase cell concentration was 30 g/L. 400 mM L-alanine and 1 mM PLP were added. The reaction temperature was controlled at 30° C. by a water bath. PPO production was detected by achiral liquid chromatography with timing sampling. Also, the decrease of D-PPT and increase and ee value of L-PPT were detected by pre-column derivatization high performance liquid chromatography.

At the end of 10 hours of reaction, 30.26 mM D-PPT remained, with conversion of 29% (the maximum theoretical conversion is 50%), 78.53 mM L-PPT was generated (99% ee), with yield of 28.5%, and less than 0.05 mM PPO formed.

Example 7

Preparation of L-Phosphinothricin Using D-Amino Acid Oxidase Mutant (E3) and Transaminase Recombinant bacteria capable of expressing D-amino acid oxidase (E3) and transaminase were cultured in the same manner as in Example 4, and the bacterial cells were collected by centrifugation.

D,L-phosphinothricin was quantitatively weighed into a 50 mM phosphate buffer with pH=8 and placed into a reactor, so that the final concentration of D,L-phosphinothricin was 100 mM, the D-amino acid oxidase (E3) cell concentration was 20 g/L, the catalase concentration was 0.1 g/L, and the transaminase cell concentration was 30 g/L. 400 mM L-alanine and 1 mM PLP were added. The reaction temperature was controlled at 30° C. by a water bath. PPO production was detected by achiral liquid chromatography with timing sampling. Also, the decrease of D-PPT and increase and ee value of L-PPT were detected by pre-column derivatization high performance liquid chromatography.

At the end of 10 hours of reaction, 21.86 mM D-PPT remained, with conversion of 37.33% (the maximum theoretical conversion is 50%), 85.47 mM L-PPT was generated (99% ee), with yield of 73%, and the residual PPO concentration was less than 0.05 mM.

Example 8

Preparation of L-Phosphinothricin Using D-Amino Acid Oxidase Mutant (E4) and Transaminase.

Recombinant bacteria capable of expressing D-amino acid oxidase (E4) and transaminase were cultured in the same manner as in Example 4, and the bacterial cells were collected by centrifugation.

D,L-phosphinothricin was quantitatively weighed into a 50 mM phosphate buffer with pH=8 and placed into a reactor, so that the final concentration of D,L-phosphinothricin was 100 mM, the D-amino acid oxidase (E4) cell concentration was 20 g/L, the catalase concentration was 0.1 g/L, and the transaminase cell concentration was 30 g/L. 400 mM L-alanine and 1 mM PLP were added. The reaction temperature was controlled at 30° C. by a water bath. PPO production was detected by achiral liquid chromatography with timing sampling. Also, the decrease of D-PPT and increase and ee value of L-PPT were detected by pre-column derivatization high performance liquid chromatography.

At the end of 10 hours of reaction, 0 mM D-PPT remained, that is, complete conversion of D-PPT was achieved, and the resulting concentration of L-PPT was 97.79 mM, i.e., yield of 94%, with ee being as high as 99%. The residual PPO concentration was less than 0.05 mM.

Example 9

Preparation of L-Phosphinothricin with High Concentration Using D-Amino Acid Oxidase Mutant (E4) and Transaminase Recombinant bacteria capable of expressing D-amino acid oxidase (E4) and transaminase were cultured in the same manner as in Example 4, and the bacterial cells were collected by centrifugation.

D,L-phosphinothricin was quantitatively weighed into 100 mM phosphate buffer with pH=8 and placed into a reactor, so that the final concentration of D,L-phosphinothricin was 400 mM, the D-amino acid oxidase (E4) cell concentration was 40 g/L, the catalase concentration was 0.1 g/L, and the transaminase cell concentration was 50 g/L. 600 mM L-alanine and 1 mM PLP were added. The reaction temperature was controlled at 30° C. by a water bath. PPO production was detected by achiral liquid chromatography with timing sampling. Also, the decrease of D-PPT and increase and ee value of L-PPT were detected by pre-column derivatization high performance liquid chromatography.

At the end of 10 hours of reaction, 0 mM D-PPT remained, that is, complete conversion of D-PPT was realized, and the resulting concentration of L-PPT was 386.79 mM with a yield of 95%, with ee of the product being as high as 99%. The residual PPO concentration was less than 0.05 mM (0.9‰).

Example 10

The L-phosphinothricin reaction mixture prepared from the D-amino acid oxidase mutant (E4) and transaminase in Example 8 was adjusted to have a pH of 5-6, and loaded onto 001x7 sodium-type or ammonium-type strong acid cation exchange resin at a flow rate of 0.5 BV/h. Alanine would be adsorbed onto the resin. After loading, the system was rinsed with ultrapure water, and L-phosphinothricin and other impurities would flow out with ultrapure water. The effluent of L-phosphinothricin was collected, and distilled under reduced pressure at 50-65° C. Then, the reaction mixture was adjusted to a pH of 2-3.5, and slowly stirred at 0-45° C. to crystallize for 1-24 hours. The treated L-phosphinothricin reaction mixture was adjusted to a pH of 1.2-2.5, and then the filtrate was loaded onto a strong acid cation exchange resin to remove a small amount of organic matters, D-type substrate and a large amount of inorganic ions, and then washed with water and eluted. The L-phosphinothricin effluent was collected, and concentrated under reduced pressure at 50-65° C. to reach a constant weight. Anhydrous methanol was added to dissolve L-phosphinothricin at 50-65° C., and then the solution was slowly stirred in an ice bath to crystallize. After stirred for 12-24 hours, the mixture was freeze-dried in a freezing vacuum dryer to obtain L-phosphinothricin crystals. The purity of the final product L-phosphinothricin reached more than 98%, and the yield reached more than 98%.

Comparative Example 1

The recombinant bacteria capable of expressing the non-mutated D-amino acid oxidase and transaminase were cultured according to the method of Example 4, and the bacterial cells were collected by centrifugation.

D,L-phosphinothricin was quantitatively weighed into a 50 mM phosphate buffer with pH=8 and placed into a reactor, so that the final concentration of D,L-phosphinothricin was 100 mM, the non-mutated D-amino acid oxidase cell concentration was 20 g/L, the catalase concentration was 0.1 g/L, and the transaminase cell concentration was 30 g/L. 400 mM L-alanine and 1 mM PLP were added. The reaction temperature was controlled at 30° C. by a water bath. PPO production was detected by achiral liquid chromatography with timed sampling. Also, the decrease of D-PPT and ee value were determined by pre-column derivatization high performance liquid chromatography.

At the end of 10 hours of reaction, 46.77 mM D-PPT remained, with conversion of 2.16% (the maximum theoretical conversion is 50%), and the total L-PTT concentration was only 53.58 mM (ee 99%), with yield of only 51.67%.

What is claimed is:

1. A method for asymmetrically preparing L-phosphinothricin by oxidation-reduction reaction through biological multi-enzyme coupling, where D,L-phosphinothricin as a raw material is catalyzed by an enzyme catalysis system to obtain L-phosphinothricin, comprising the step of catalyzing D-phosphinothricin in D,L-phosphinothricin into 2-carbonyL-4-[hydroxy(methyl)phosphono] butyric acid by a D-amino acid oxidase mutant of the enzyme catalysis system and catalytically reducing the 2-carbonyl-4-[hydroxy (methyl)phosphono] butyric acid into L-phosphinothricin by a transaminase of the enzyme catalysis system, and wherein the D-amino acid oxidase mutant is obtained by mutation of D-amino acid oxidase in wild strain *Rhodotorula taiwanensis* at one of the following sites:
(a) M213S-N54V-F58E-D207A;
(b) M213S-N54V-F58E-D207A-S60T.

2. The method according to claim 1, wherein the transaminase has the amino acid sequence as shown in SEQ ID NO: 39.

3. The method according to claim 2, wherein the D-amino acid oxidase mutant is obtained by adding a genetically engineered bacterium expressing the D-amino acid oxidase mutant into a reaction system; and the transaminase is obtained by adding a genetically engineered bacterium expressing the transaminase together with a coenzyme pyridoxal phosphate into the reaction system.

4. The method according to claim 3, wherein *E. coli* BL21 (DE3) is used as a host cell for both of the genetically engineered bacteria.

5. The method according to claim 3, wherein in the reaction system, the D,L-phosphinothricin has a final concentration of 100-400 mM, the genetically engineered bacterium expressing the D-amino acid oxidase mutant is added at an amount of 20-40 g/L, the genetically engineered bacterium expressing the transaminase is added at an amount of 30-50 g/L, and the coenzyme pyridoxal phosphate has a concentration of 1 mM.

6. The method according to claim 5, wherein the reaction is carried out at a temperature of 30° C. and a pH of 8 for 10 hours.

7. The method according to claim 6, wherein after the reaction is completed, the final product L-phosphinothricin is separated and extracted by ion exchange and crystallization.

8. A D-amino acid oxidase mutant obtained by mutation of a D-amino acid oxidase in wild-type *Rhodotorula taiwanensis* at one of the following sites:

(a) M213S-N54V-F58E-D207A;

(b) M213S-N54V-F58E-D207A-S60T.

9. A gene encoding the D-amino acid oxidase mutant according to claim 8, wherein the gene has the nucleotide sequence of SEQ ID NO: 5 or SEQ ID NO: 6.

10. A genetically engineered bacterium comprising the gene according to claim 9.

* * * * *

SEQUENCE LISTING

<160> NUMBER OF SEQ ID NOS: 41

<210> SEQ ID NO 1
<211> LENGTH: 372
<212> TYPE: PRT
<213> ORGANISM: Rhodotorula taiwanensis

<400> SEQUENCE: 1

```
Met Ala Pro Ser Lys Arg Val Val Leu Gly Ser Gly Val Val Gly
1               5                   10                  15

Leu Ser Ser Ala Leu Thr Leu Ala Gln Lys Gly Tyr Ser Val His Val
            20                  25                  30

Val Ala Arg Asp Leu Pro Glu Asp Thr Val Ala Gln Thr Phe Ala Ser
        35                  40                  45

Pro Trp Ala Gly Ala Asn Trp Thr Pro Phe Met Ser Lys Glu Asp Gly
    50                  55                  60

Pro Arg Gln Ala Lys Trp Glu Thr Ala Thr Phe Asn Gln Trp Val Asp
65                  70                  75                  80

Leu Val Pro Gln Gly Leu Ala Met Trp Leu Lys Gly Thr Arg Arg Tyr
                85                  90                  95

Ala Gln Asp Glu Ala Gly Leu Leu Gly His Trp Tyr Gln His Ile Thr
            100                 105                 110

Pro Asn Tyr Arg Lys Leu Glu Ser Ser Glu Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Glu Gly Gly Phe Asp Leu Ile Val
                165                 170                 175
```

```
Asn Ala Thr Gly Leu Gly Ala Lys Ser Ile Ala Gly Val Glu Asp Gln
            180                 185                 190
Glu Val Glu Pro Ile Arg Gly Gln Thr Val Leu Val Lys Ser Asp Cys
        195                 200                 205
Lys Arg Cys Thr Met Asp Ser Ser Asp Pro Asn Ser Pro Ala Tyr Ile
210                 215                 220
Ile Pro Arg Pro Gly Gly Glu Val Ile Cys Gly Thr Tyr Leu Val
225                 230                 235                 240
Gly Asn Tyr Asp Leu Ser Val Asp Pro Pro Thr Ile Asn Arg Ile Leu
            245                 250                 255
Gln His Cys Leu Arg Leu Asp Pro Ser Ile Ser Thr Asp Gly Thr Leu
        260                 265                 270
Glu Gly Ile Glu Ile Val Arg His Asn Val Gly Leu Arg Pro Ala Arg
    275                 280                 285
Arg Gly Gly Pro Arg Val Glu Val Glu Arg Val Ala Phe Pro Leu Glu
290                 295                 300
Arg Gly Lys Ser Lys Leu Ser Leu Gly Thr Ala Arg Ala Asp Ser Ser
305                 310                 315                 320
Lys Pro Arg Arg Glu Val Pro Val Val His Ala Tyr Gly Phe Ser Ser
            325                 330                 335
Ala Gly Tyr Gln Gln Gly Trp Gly Ala Ala Leu Glu Val Ala Glu Leu
        340                 345                 350
Val Glu Gly Ala Ile Gly Ala Ala Pro Ala Arg Ser Ser His Arg Trp
    355                 360                 365
Leu Ser Lys Leu
    370

<210> SEQ ID NO 2
<211> LENGTH: 1116
<212> TYPE: DNA
<213> ORGANISM: Artificial Sequence
<220> FEATURE:
<223> OTHER INFORMATION: Synthesized

<400> SEQUENCE: 2
atggcgccga gcaagcgtgt ggttgtgctg ggtagcggcg ttgttggtct gagcagcgcg      60
ctgaccctgg cgcagaaagg ctacagcgtt cacgttgtgg cgcgtgacct gccggaagat     120
accgttgcgc aaacctttgc gagcccgtgg gcgggtgcga actggacccc gtttatgagc     180
aaggaagacg tccgcgtca ggcgaaatgg gagaccgcga cctttaacca gtgggttgat     240
ctggtgccgc aaggtctggc gatgtggctg aagggcaccc gtcgttatgc gcaagatgag     300
gcgggtctgc tggtcactg gtaccaacac atcaccccga actatcgtaa actggagagc     360
agcgaatgcc cgccgggtgc gattggtgtt acctacgata ccctgagcgt gaacgcgccg     420
aagttctgcc agtatctgca acgtgaagcg cagaaactgg tgttaccctt gagcgtcgt     480 ctggtgacca gcctggagca aatcgaaggt ggcttcgacc tgattgttaa cgcgaccggt     540
ctgggtgcga agagcattgc gggtgttgaa gaccaggaag tggaaccgat cgtggccaa     600 accgttctgg tgaagagcga ttgcaaacgt tgcaccatgg acagcagcga tccgaacagc     660
ccggcgtaca tcattccgcg tccgggtggc gaggtgatct gcggtggcac ctacctggtt     720
ggtaactatg acctgagcgt ggatccgccg accatcaacc gtattctgca gcactgcctg     780
cgtctggacc cgagcattag caccgatggt accctgagg gcatcgaaat tgttcgtcat     840
aacgttggcc tgcgtccggc gcgtcgtggt ggcccgcgtg ttgaggtgga acgtgttgcg     900
```

| | | |
|---|---|---|
| tttccgctgg aacgtggcaa gagcaaactg agcctgggta ccgcgcgtgc ggatagcagc | 960 |
| aaaccgcgtc gtgaggtgcc ggttgtgcac gcgtacggtt tcagcagcgc gggttatcaa | 1020 |
| cagggttggg gcgcggcgct ggaagtggcg gaactggtgg agggtgcgat tggtgcggcg | 1080 |
| ccggcgcgta gcagccaccg ttggctgagc aaactg | 1116 |

<210> SEQ ID NO 3
<211> LENGTH: 1116
<212> TYPE: DNA
<213> ORGANISM: Artificial Sequence
<220> FEATURE:
<223> OTHER INFORMATION: Synthesized

<400> SEQUENCE: 3

| | | |
|---|---|---|
| atggcgccga gcaagcgtgt ggttgtgctg ggtagcggcg ttgttggtct gagcagcgcg | 60 |
| ctgaccctgg cgcagaaagg ctacagcgtt cacgttgtgg cgcgtgacct gccggaagat | 120 |
| accgttgcgc aaacctttgc gagcccgtgg gcgggtgcga actggacccc gtttatgagc | 180 |
| aaggaagacg gtccgcgtca ggcgaaatgg gagaccgcga cctttaacca gtgggttgat | 240 |
| ctggtgccga aggtctggc gatgtggctg aagggcaccc gtcgttatgc gcaagatgag | 300 |
| gcgggtctgc tgggtcactg gtaccaacac atcaccccga actatcgtaa actggagagc | 360 |
| agcgaatgcc cgccgggtgc gattggtgtt acctacgata ccctgagcgt gaacgcgccg | 420 |
| aagttctgcc agtatctgca acgtgaagcg cagaaactgg gtgttacctt tgagcgtcgt | 480 |
| ctggtgacca gcctggagca aatcgaaggt ggcttcgacc tgattgttaa cgcgaccggt | 540 |
| ctgggtgcga agagcattgc gggtgttgaa gaccaggaag tggaaccgat tcgtggccaa | 600 |
| accgttctgg tgaagagcga ttgcaaacgt tgcacctctg acagcagcga tccgaacagc | 660 |
| ccggcgtaca tcattccgcg tccgggtggc gaggtgatct gcggtggcac ctacctggtt | 720 |
| ggtaactatg acctgagcgt ggatccgccg accatcaacc gtattctgca gcactgcctg | 780 |
| cgtctggacc cgagcattag caccgatggt accctggagg gcatcgaaat tgttcgtcat | 840 |
| aacgttggcc tgcgtccggc gcgtcgtggt ggcccgcgtg ttgaggtgga acgtgttgcg | 900 |
| tttccgctgg aacgtggcaa gagcaaactg agcctgggta ccgcgcgtgc ggatagcagc | 960 |
| aaaccgcgtc gtgaggtgcc ggttgtgcac gcgtacggtt tcagcagcgc gggttatcaa | 1020 |
| cagggttggg gcgcggcgct ggaagtggcg gaactggtgg agggtgcgat tggtgcggcg | 1080 |
| ccggcgcgta gcagccaccg ttggctgagc aaactg | 1116 |

<210> SEQ ID NO 4
<211> LENGTH: 1116
<212> TYPE: DNA
<213> ORGANISM: Artificial Sequence
<220> FEATURE:
<223> OTHER INFORMATION: Synthesized

<400> SEQUENCE: 4

| | | |
|---|---|---|
| atggcgccga gcaagcgtgt ggttgtgctg ggtagcggcg ttgttggtct gagcagcgcg | 60 |
| ctgaccctgg cgcagaaagg ctacagcgtt cacgttgtgg cgcgtgacct gccggaagat | 120 |
| accgttgcgc aaacctttgc gagcccgtgg gcgggtgcga tttggacccc ggaaatgagc | 180 |
| aaggaagacg gtccgcgtca ggcgaaatgg gagaccgcga cctttaacca gtgggttgat | 240 |
| ctggtgccga aggtctggc gatgtggctg aagggcaccc gtcgttatgc gcaagatgag | 300 |
| gcgggtctgc tgggtcactg gtaccaacac atcaccccga actatcgtaa actggagagc | 360 |

| | |
|---|---|
| agcgaatgcc cgccgggtgc gattggtgtt acctacgata ccctgagcgt gaacgcgccg | 420 |
| aagttctgcc agtatctgca acgtgaagcg cagaaactgg gtgttacctt tgagcgtcgt | 480 |
| ctggtgacca gcctggagca aatcgaaggt ggcttcgacc tgattgttaa cgcgaccggt | 540 |
| ctgggtgcga agagcattgc gggtgttgaa gaccaggaag tggaaccgat tcgtggccaa | 600 |
| accgttctgg tgaagagcga ttgcaaacgt tgcacctctg acagcagcga tccgaacagc | 660 |
| ccggcgtaca tcattccgcg tccgggtggc gaggtgatct gcggtggcac ctacctggtt | 720 |
| ggtaactatg acctgagcgt ggatccgccg accatcaacc gtattctgca gcactgcctg | 780 |
| cgtctggacc cgagcattag caccgatggt accctggagg catcgaaat tgttcgtcat | 840 |
| aacgttggcc tgcgtccggc gcgtcgtggt ggcccgcgtg ttgaggtgga acgtgttgcg | 900 |
| tttccgctgg aacgtggcaa gagcaaactg agcctgggta ccgcgcgtgc ggatagcagc | 960 |
| aaaccgcgtc gtgaggtgcc ggttgtgcac gcgtacggtt tcagcagcgc gggttatcaa | 1020 |
| cagggttggg gcgcggcgct ggaagtggcg gaactggtgg agggtgcgat tggtgcggcg | 1080 |
| ccggcgcgta gcagccaccg ttggctgagc aaactg | 1116 |

<210> SEQ ID NO 5
<211> LENGTH: 1116
<212> TYPE: DNA
<213> ORGANISM: Artificial Sequence
<220> FEATURE:
<223> OTHER INFORMATION: Synthesized

<400> SEQUENCE: 5

| | |
|---|---|
| atggcgccga gcaagcgtgt ggttgtgctg ggtagcggcg ttgttggtct gagcagcgcg | 60 |
| ctgaccctgg cgcagaaagg ctacagcgtt cacgttgtgg cgcgtgacct gccggaagat | 120 |
| accgttgcgc aaacctttgc gagcccgtgg gcgggtgcgg tttggaccc ggaaatgagc | 180 |
| aaggaagacg gtccgcgtca ggcgaaatgg gagaccgcga cctttaacca gtgggttgat | 240 |
| ctggtgccga aggtctggc gatgtggctg aagggcaccc gtcgttatgc gcaagatgag | 300 |
| gcgggtctgc tgggtcactg gtaccaacac atcaccccga actatcgtaa actggagagc | 360 |
| agcgaatgcc cgccgggtgc gattggtgtt acctacgata ccctgagcgt gaacgcgccg | 420 |
| aagttctgcc agtatctgca acgtgaagcg cagaaactgg gtgttacctt tgagcgtcgt | 480 |
| ctggtgacca gcctggagca aatcgaaggt ggcttcgacc tgattgttaa cgcgaccggt | 540 |
| ctgggtgcga agagcattgc gggtgttgaa gaccaggaag tggaaccgat tcgtggccaa | 600 |
| accgttctgg tgaagagcgc ttgcaaacgt tgcacctctg acagcagcga tccgaacagc | 660 |
| ccggcgtaca tcattccgcg tccgggtggc gaggtgatct gcggtggcac ctacctggtt | 720 |
| ggtaactatg acctgagcgt ggatccgccg accatcaacc gtattctgca gcactgcctg | 780 |
| cgtctggacc cgagcattag caccgatggt accctggagg catcgaaat tgttcgtcat | 840 |
| aacgttggcc tgcgtccggc gcgtcgtggt ggcccgcgtg ttgaggtgga acgtgttgcg | 900 |
| tttccgctgg aacgtggcaa gagcaaactg agcctgggta ccgcgcgtgc ggatagcagc | 960 |
| aaaccgcgtc gtgaggtgcc ggttgtgcac gcgtacggtt tcagcagcgc gggttatcaa | 1020 |
| cagggttggg gcgcggcgct ggaagtggcg gaactggtgg agggtgcgat tggtgcggcg | 1080 |
| ccggcgcgta gcagccaccg ttggctgagc aaactg | 1116 |

<210> SEQ ID NO 6
<211> LENGTH: 1116
<212> TYPE: DNA
<213> ORGANISM: Artificial Sequence

```
<220> FEATURE:
<223> OTHER INFORMATION: Synthesized

<400> SEQUENCE: 6
atggcgccga gcaagcgtgt ggttgtgctg ggtagcggcg ttgttggtct gagcagcgcg      60
ctgaccctgg cgcagaaagg ctacagcgtt cacgttgtgg cgcgtgacct gccggaagat     120
accgttgcgc aaacctttgc gagcccgtgg gcgggtgcgg tttggacccc ggaaatgacc     180
aaggaagacg gtccgcgtca ggcgaaatgg gagaccgcga cctttaacca gtgggttgat     240
ctggtgccgc aaggtctggc gatgtggctg aagggcaccc gtcgttatgc gcaagatgag     300
gcgggtctgc tgggtcactg gtaccaacac atcaccccga actatcgtaa actggagagc     360
agcgaatgcc cgccgggtgc gattggtgtt acctacgata ccctgagcgt gaacgcgccg     420
aagttctgcc agtatctgca acgtgaagcg cagaaactgg tgttaccttt gagcgtcgt      480 ctggtgacca gcctggagca aatcgaaggt ggcttcgacc tgattgttaa cgcgaccggt     540
ctgggtgcga gagcattgc gggtgttgaa gaccaggaag tggaaccgat cgtggccaa       600 accgttctgg tgaagagcgc ttgcaaacgt tgcacctctg acagcagcga tccgaacagc     660
ccggcgtaca tcattccgcg tccgggtggc gaggtgatct gcggtggcac ctacctggtt     720
ggtaactatg acctgagcgt ggatccgccg accatcaacc gtattctgca gcactgcctg     780
cgtctggacc cgagcattag caccgatggt accctgagg gcatcgaaat tgttcgtcat      840
aacgttggcc tgcgtccggc gcgtcgtggt ggcccgcgtg ttgaggtgga acgtgttgcg     900
tttccgctgg aacgtggcaa gagcaaactg agcctgggta ccgcgcgtgc ggatagcagc     960
aaaccgcgtc gtgaggtgcc ggttgtgcac gcgtacggtt tcagcagcgc gggttatcaa    1020
cagggttggg gcgcggcgct ggaagtggcg gaactggtgg aggtgcgat tggtgcggcg      1080 ccggcgcgta gcagccaccg ttggctgagc aaactg                               1116

<210> SEQ ID NO 7
<211> LENGTH: 30
<212> TYPE: DNA
<213> ORGANISM: Artificial Sequence
<220> FEATURE:
<223> OTHER INFORMATION: Synthesized

<400> SEQUENCE: 7
cgttgcacct ctgacagcag cgatccgaac                                       30

<210> SEQ ID NO 8
<211> LENGTH: 28
<212> TYPE: DNA
<213> ORGANISM: Artificial Sequence
<220> FEATURE:
<223> OTHER INFORMATION: Synthesized

<400> SEQUENCE: 8
cgctgctgtc agaggtgcaa cgtttgca                                         28

<210> SEQ ID NO 9
<211> LENGTH: 30
<212> TYPE: DNA
<213> ORGANISM: Artificial Sequence
<220> FEATURE:
<223> OTHER INFORMATION: Synthesized

<400> SEQUENCE: 9
cgttgcaccc gtgacagcag cgatccgaac                                       30
```

```
<210> SEQ ID NO 10
<211> LENGTH: 28
<212> TYPE: DNA
<213> ORGANISM: Artificial Sequence
<220> FEATURE:
<223> OTHER INFORMATION: Synthesized

<400> SEQUENCE: 10
cgctgctgtc acgggtgcaa cgtttgca                                        28

<210> SEQ ID NO 11
<211> LENGTH: 35
<212> TYPE: DNA
<213> ORGANISM: Artificial Sequence
<220> FEATURE:
<223> OTHER INFORMATION: Synthesized

<400> SEQUENCE: 11
cgggtgcggt ttggaccccg gaaatgagca aggaa                                35

<210> SEQ ID NO 12
<211> LENGTH: 35
<212> TYPE: DNA
<213> ORGANISM: Artificial Sequence
<220> FEATURE:
<223> OTHER INFORMATION: Synthesized

<400> SEQUENCE: 12
atttccgggg tccaaaccgc acccgcccac gggct                                35

<210> SEQ ID NO 13
<211> LENGTH: 35
<212> TYPE: DNA
<213> ORGANISM: Artificial Sequence
<220> FEATURE:
<223> OTHER INFORMATION: Synthesized

<400> SEQUENCE: 13
cgggtgcggg ttggaccccg gaaatgagca aggaa                                35

<210> SEQ ID NO 14
<211> LENGTH: 35
<212> TYPE: DNA
<213> ORGANISM: Artificial Sequence
<220> FEATURE:
<223> OTHER INFORMATION: Synthesized

<400> SEQUENCE: 14
atttccgggg tccaacccgc acccgcccac gggct                                35

<210> SEQ ID NO 15
<211> LENGTH: 35
<212> TYPE: DNA
<213> ORGANISM: Artificial Sequence
<220> FEATURE:
<223> OTHER INFORMATION: Synthesized

<400> SEQUENCE: 15
cgggtgcgct ttggaccccg gaaatgagca aggaa                                35

<210> SEQ ID NO 16
<211> LENGTH: 35
<212> TYPE: DNA
<213> ORGANISM: Artificial Sequence
<220> FEATURE:
<223> OTHER INFORMATION: Synthesized
```

<400> SEQUENCE: 16
atttccgggg tccaaagcgc acccgcccac gggct                35

<210> SEQ ID NO 17
<211> LENGTH: 35
<212> TYPE: DNA
<213> ORGANISM: Artificial Sequence
<220> FEATURE:
<223> OTHER INFORMATION: Synthesized

<400> SEQUENCE: 17
cgggtgcggc ttggaccccg gaaatgagca aggaa                35

<210> SEQ ID NO 18
<211> LENGTH: 35
<212> TYPE: DNA
<213> ORGANISM: Artificial Sequence
<220> FEATURE:
<223> OTHER INFORMATION: Synthesized

<400> SEQUENCE: 18
atttccgggg tccaagccgc acccgcccac gggct                35

<210> SEQ ID NO 19
<211> LENGTH: 27
<212> TYPE: DNA
<213> ORGANISM: Artificial Sequence
<220> FEATURE:
<223> OTHER INFORMATION: Synthesized

<400> SEQUENCE: 19
gaccccggaa atgagcaagg aagacgg                27

<210> SEQ ID NO 20
<211> LENGTH: 27
<212> TYPE: DNA
<213> ORGANISM: Artificial Sequence
<220> FEATURE:
<223> OTHER INFORMATION: Synthesized

<400> SEQUENCE: 20
cttgctcatt tccggggtcc aaaccgc                27

<210> SEQ ID NO 21
<211> LENGTH: 27
<212> TYPE: DNA
<213> ORGANISM: Artificial Sequence
<220> FEATURE:
<223> OTHER INFORMATION: Synthesized

<400> SEQUENCE: 21
gaccccggct atgagcaagg aagacgg                27

<210> SEQ ID NO 22
<211> LENGTH: 27
<212> TYPE: DNA
<213> ORGANISM: Artificial Sequence
<220> FEATURE:
<223> OTHER INFORMATION: Synthesized

<400> SEQUENCE: 22
cttgctcata gccggggtcc aaaccgc                27

<210> SEQ ID NO 23

```
<211> LENGTH: 27
<212> TYPE: DNA
<213> ORGANISM: Artificial Sequence
<220> FEATURE:
<223> OTHER INFORMATION: Synthesized

<400> SEQUENCE: 23
gaccccgcgt atgagcaagg aagacgg                                              27

<210> SEQ ID NO 24
<211> LENGTH: 27
<212> TYPE: DNA
<213> ORGANISM: Artificial Sequence
<220> FEATURE:
<223> OTHER INFORMATION: Synthesized

<400> SEQUENCE: 24
cttgctcata cgcggggtcc aaaccgc                                              27

<210> SEQ ID NO 25
<211> LENGTH: 27
<212> TYPE: DNA
<213> ORGANISM: Artificial Sequence
<220> FEATURE:
<223> OTHER INFORMATION: Synthesized

<400> SEQUENCE: 25
gaccccgtcg atgagcaagg aagacgg                                              27

<210> SEQ ID NO 26
<211> LENGTH: 27
<212> TYPE: DNA
<213> ORGANISM: Artificial Sequence
<220> FEATURE:
<223> OTHER INFORMATION: Synthesized

<400> SEQUENCE: 26
cttgctcatc gacggggtcc aaaccgc                                              27

<210> SEQ ID NO 27
<211> LENGTH: 30
<212> TYPE: DNA
<213> ORGANISM: Artificial Sequence
<220> FEATURE:
<223> OTHER INFORMATION: Synthesized

<400> SEQUENCE: 27
gtgaagagcg cttgcaaacg ttgcacctct                                           30

<210> SEQ ID NO 28
<211> LENGTH: 29
<212> TYPE: DNA
<213> ORGANISM: Artificial Sequence
<220> FEATURE:
<223> OTHER INFORMATION: Synthesized

<400> SEQUENCE: 28
caacgtttgc aagcgctctt caccagaac                                            29

<210> SEQ ID NO 29
<211> LENGTH: 30
<212> TYPE: DNA
<213> ORGANISM: Artificial Sequence
<220> FEATURE:
<223> OTHER INFORMATION: Synthesized

<400> SEQUENCE: 29
```
gtgaagagca cgtgcaaacg ttgcacctct                                              30

<210> SEQ ID NO 30
<211> LENGTH: 29
<212> TYPE: DNA
<213> ORGANISM: Artificial Sequence
<220> FEATURE:
<223> OTHER INFORMATION: Synthesized

<400> SEQUENCE: 30
caacgtttgc acgtgctctt caccagaac                                               29

<210> SEQ ID NO 31
<211> LENGTH: 30
<212> TYPE: DNA
<213> ORGANISM: Artificial Sequence
<220> FEATURE:
<223> OTHER INFORMATION: Synthesized

<400> SEQUENCE: 31
gtgaagagcg agtgcaaacg ttgcacctct                                              30

<210> SEQ ID NO 32
<211> LENGTH: 29
<212> TYPE: DNA
<213> ORGANISM: Artificial Sequence
<220> FEATURE:
<223> OTHER INFORMATION: Synthesized

<400> SEQUENCE: 32
caacgtttgc actcgctctt caccagaac                                               29

<210> SEQ ID NO 33
<211> LENGTH: 30
<212> TYPE: DNA
<213> ORGANISM: Artificial Sequence
<220> FEATURE:
<223> OTHER INFORMATION: Synthesized

<400> SEQUENCE: 33
ccggaaatga ctaaggaaga cggtccgcgt                                              30

<210> SEQ ID NO 34
<211> LENGTH: 30
<212> TYPE: DNA
<213> ORGANISM: Artificial Sequence
<220> FEATURE:
<223> OTHER INFORMATION: Synthesized

<400> SEQUENCE: 34
gtcttcctta gtcatttccg gggtccaaac                                              30

<210> SEQ ID NO 35
<211> LENGTH: 30
<212> TYPE: DNA
<213> ORGANISM: Artificial Sequence
<220> FEATURE:
<223> OTHER INFORMATION: Synthesized

<400> SEQUENCE: 35
ccggaaatgg ctaaggaaga cggtccgcgt                                              30

<210> SEQ ID NO 36
<211> LENGTH: 30
<212> TYPE: DNA

```
<213> ORGANISM: Artificial Sequence
<220> FEATURE:
<223> OTHER INFORMATION: Synthesized

<400> SEQUENCE: 36
gtcttcctta gccatttccg gggtccaaac                                                30

<210> SEQ ID NO 37
<211> LENGTH: 30
<212> TYPE: DNA
<213> ORGANISM: Artificial Sequence
<220> FEATURE:
<223> OTHER INFORMATION: Synthesized

<400> SEQUENCE: 37
ccggaaatgg agaaggaaga cggtccgcgt                                                30

<210> SEQ ID NO 38
<211> LENGTH: 30
<212> TYPE: DNA
<213> ORGANISM: Artificial Sequence
<220> FEATURE:
<223> OTHER INFORMATION: Synthesized

<400> SEQUENCE: 38
gtcttccttc tccatttccg gggtccaaac                                                30

<210> SEQ ID NO 39
<211> LENGTH: 425
<212> TYPE: PRT
<213> ORGANISM: Pseudomonas fluorescens

<400> SEQUENCE: 39
```

Met Ser Lys Asn Glu Ser Leu Leu Gln Arg Arg Gln Ala Ala Val Ala
1               5                   10                  15

Arg Gly Val Ser Gln Ile His Pro Ile Val Ala Glu Arg Ala Glu Asn
                20                  25                  30

Ala Thr Val Trp Asp Val Asp Gly Arg Glu Tyr Ile Asp Phe Ala Gly
            35                  40                  45

Gly Ile Ala Val Leu Asn Thr Gly His Leu His Pro Lys Val Ile Ala
        50                  55                  60

Ala Val Gln Glu Gln Leu Thr Lys Leu Thr His Thr Cys Phe Gln Val
65                  70                  75                  80

Leu Ala Tyr Glu Pro Tyr Ile Ala Leu Cys Glu Glu Ile Ala Lys Arg
                85                  90                  95

Val Pro Gly Asp Phe Ala Lys Lys Thr Leu Leu Val Thr Ser Gly Ser
                100                 105                 110

Glu Ala Val Glu Asn Ala Val Lys Ile Ala Arg Ala Ala Thr Gly Arg
            115                 120                 125

Ala Gly Val Ile Ala Phe Thr Gly Ala Tyr His Gly Arg Thr Met Met
        130                 135                 140

Thr Leu Ser Leu Thr Gly Lys Val Val Pro Tyr Ser Ala Gly Met Gly
145                 150                 155                 160

Leu Met Pro Gly Gly Val Phe Arg Ala Leu Ala Pro Cys Pro Leu His
                165                 170                 175

Gly Ile Ser Glu Asp Glu Ser Ile Ala Ser Ile Glu Arg Ile Phe Lys
                180                 185                 190

Asn Asp Ala Gln Pro Arg Asp Ile Ala Ala Ile Ile Ile Glu Pro Val
            195                 200                 205

```
Gln Gly Glu Gly Gly Phe Tyr Val Asn Ser Pro Ala Phe Met Lys Arg
    210                 215                 220

Leu Arg Ala Leu Cys Asp Glu His Gly Ile Leu Leu Ile Ala Asp Glu
225                 230                 235                 240

Val Gln Thr Gly Ala Gly Arg Thr Gly Thr Phe Phe Ala Thr Glu Gln
            245                 250                 255

Leu Gly Ile Val Pro Asp Leu Thr Thr Phe Ala Lys Ser Val Gly Gly
            260                 265                 270

Gly Phe Pro Ile Ser Gly Val Cys Gly Lys Ala Glu Ile Met Asp Ser
        275                 280                 285

Ile Ala Pro Gly Gly Leu Gly Gly Thr Tyr Ala Gly Ser Pro Ile Ala
    290                 295                 300

Cys Ala Ala Leu Ala Val Met Glu Val Phe Glu Glu Glu Lys Leu
305                 310                 315                 320

Leu Glu Arg Ser Gln Ala Leu Gly Glu Lys Leu Lys Ala Gly Leu Asn
                325                 330                 335

Ala Ile Ala Ala Lys His Lys Val Ile Gly Asp Val Arg Gly Leu Gly
            340                 345                 350

Ser Met Val Ala Ile Glu Leu Phe Glu Gly Gly Asp His Asn Lys Pro
        355                 360                 365

Ala Ala Glu Leu Val Gly Lys Ile Val Ala Arg Ala Arg Glu Lys Gly
    370                 375                 380

Leu Ile Leu Leu Ser Cys Gly Thr Tyr Tyr Asn Val Ile Arg Phe Leu
385                 390                 395                 400

Met Pro Val Thr Ile Pro Asp Ala Gln Leu Glu Lys Gly Ile Ala Ile
            405                 410                 415

Val Ala Glu Cys Phe Asp Glu Leu Ala
            420                 425

<210> SEQ ID NO 40
<211> LENGTH: 19
<212> TYPE: DNA
<213> ORGANISM: Artificial Sequence
<220> FEATURE:
<223> OTHER INFORMATION: Synthesized

<400> SEQUENCE: 40
atgaacacca acaacgctc                                                    19

<210> SEQ ID NO 41
<211> LENGTH: 18
<212> TYPE: DNA
<213> ORGANISM: Artificial Sequence
<220> FEATURE:
<223> OTHER INFORMATION: Synthesized

<400> SEQUENCE: 41
ttaagcctgt ttagcttc                                                     18
```